(12) United States Patent
Campbell

(10) Patent No.: US 6,200,340 B1
(45) Date of Patent: Mar. 13, 2001

(54) TILTING DISK HEART VALVE HAVING CAVITATION REDUCING CONTACT GEOMETRY

(75) Inventor: Louis A. Campbell, Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/284,000

(22) Filed: Apr. 1, 1999

(51) Int. Cl.$^7$ ........................................ A61F 2/24
(52) U.S. Cl. ............................................. 623/2.33
(58) Field of Search .................... 623/2.2, 2.22, 623/2.33, 2.35

(56) References Cited

U.S. PATENT DOCUMENTS

| | | | |
|---|---|---|---|
| 3,476,143 | 11/1969 | Kaster | 137/527.8 |
| 3,698,018 | 10/1972 | Shiley | 3/1 |
| 3,725,961 | 4/1973 | Magovern et al. | 3/1 |
| 4,276,658 | 7/1981 | Hanson et al. | 3/1.5 |
| 4,443,894 | 4/1984 | Klawitter | 3/1.5 |
| 4,689,046 | 8/1987 | Bokros | 623/2 |
| 4,846,830 | * 7/1989 | Knoch . | |
| 5,147,390 | 9/1992 | Campbell | 623/2 |
| 5,171,263 | * 12/1992 | Boyer | 623/2.2 |
| 5,824,062 | 10/1998 | Patke et al. | 623/2 |

* cited by examiner

Primary Examiner—Michael J. Milano
(74) Attorney, Agent, or Firm—Timothy L. Scott; Philip S. Lyren

(57) ABSTRACT

A heart valve prosthesis includes a valve housing having an opening formed therein having an inmost arcuate surface and a leaflet pivotally mounted in the opening for movement between an open position and a closed position with the inmost arcuate surface. The leaflet has an outmost edge providing multiple points of contact with the housing. The leaflet also forms a leakage gap adjacent the leaflet major radius and between the inmost and outmost surfaces such that the multiple points of contact are displaced from the leaflet major radius and are adjacent to and on opposite sides of the leakage gap. One or several such leaflets may be provided in the housing. Each leaflet respectively includes the leakage gap and the adjacent multiple points of contact.

10 Claims, 2 Drawing Sheets

TILTING DISK HEART VALVE HAVING CAVITATION REDUCING CONTACT GEOMETRY

BACKGROUND

The disclosures herein relate generally to a heart valve prosthesis particularly to a tilting disc valve having one or more leaflets.

Tilting disk valves have an advantage over translating disk valves in that the side profile of a tilting disk or leaflet is thin and unobstructive when rotated to the open position compared to the translating disk or ball type valve. The minimally obstructed passage of blood through an open tilting leaflet valve reduces the amount of work required by the human heart employing such a valve.

An example of a translating disk valve is disclosed in U.S. Pat. No. 3,725,961 wherein a prosthetic heart valve is disclosed having a support ring which carries means for retaining a movable closure element in positions adjacent one side of the ring. The support ring has a fabric wrapping which defines, as a suturing element, an annular protrusion of fabric of double thickness extending from the side of the ring which is opposite the side adjacent the closure element.

U.S. Pat. No. 3,476,143 discloses a one-way mechanical heart valve comprising a base having a passage allowing liquid to flow through the valve. A disc located within the passage pivots about a chordal axis to an open position and a closed position relative to a seat on the inside of the base. In one form the seat includes an inclined upper arcuate seat and an inclined lower arcuate seat circumventing the passage. In another form, the seat is an annular portion of the internal annular wall which is engaged by the periphery of the disc. Two pairs of circumferentially spaced pivot projections provide for the pivoting of the disc about a cordial axis of the disc. Retaining means in the form of curved side ears or a center strut hold the disc in assembled relation with the base.

U.S. Pat. No. 3,698,018 discloses a heart valve prosthesis having a discoid poppet mounted therein for pivotal movement between a closed and opened position. The poppet is supported for movement by opposed, spaced support struts which form an eccentric pivot point for opening of the valve and a changing pivot point for closing of the valve. The spacing between the struts is sufficient to enable rotational movement of the poppet during operation.

U.S. Pat. No. 4,276,658 discloses a heart valve prosthesis coated in its entirety with pyrolytic carbon. The prosthesis is formed of a base having a blood passageway and dual leaflets pivotally secured to the base to regulate the flow of blood through the passageway. The pivot connection between the base and leaflets is formed by recesses in the base and projections on the leaflets, the recesses and projection termini being formed as surfaces of revolution. The valve is assembled by elastically deforming the base to allow insertion of the projections within the recesses.

U.S. Pat. No. 4,443,894 discloses a heart valve having a pair of leaflets which are supported by respective floating pivots. The pivots guide the leaflets between open and closed positions due to the leaflets being pivotally mounted in dog-leg shaped depressions. The depressions each have a downstream section which angles outward from a centerline plane of the valve body and a connected vertical upstream section. In the closed position, the guides reside in intermediate portions of the depressions to unload wear forces between the guides and the depression walls for reducing wear on the pivot points.

U.S. Pat. No. 4,689,046 discloses a heart valve prosthesis with an annular body portion and at least one valve leaflet moveable between open, closed, and intermediate positions. The body includes leaflet ear support formations, each with a contoured recess having spaced apart convex ear support surfaces. Each valve leaflet includes mounting ears with upper and lower support surfaces of generally trapezoidal outline, a generally flat end face portion, and two spaced apart guide surface portions tapered so as to lie in closely spaced apart relation to the tapered guide walls in the recess.

U.S. Pat. No. 5,147,390 discloses a bi-leaflet heart valve having an annular body and a pair of leaflets. The leaflets pivot around improved ears, whose motion is constrained by generally triangular recesses. The triangular recesses have a pivotal vertex in proximity to a centerline of the annular base and on the upstream side of the heart valve. Opposite the pivotal vertex is a slightly convex base. The opening angle of the leaflets can be adjusted by varying the inclination of a wall of the triangular recess adjacent the center line. The opening angle should be adjusted, according to the teachings of the present invention, to minimize energy loss for a particular inside diameter of the heart valve. The optimum opening angle can be determined by in vitro testing using an adjustable valve and a pulse duplicator.

U.S. Pat. No. 5,824,062 discloses a bi-leaflet heart valve including an annular base and pivoting leaflets. Each leaflet is "free-floating" within recesses without fixed rotational axes, to increase translational movement and redistribute stresses. Each recess fluidly communicates with a groove extending at least partially around the inner surface of the annular base and flow is directed through the recesses at different angles during antegrade circulation, retrograde circulation, and valve closure. A recess entrance angle to each of the recesses is preferably less than about 35°, and the pivoting mechanism within the recess includes first and second fulcrum edges of each leaflet shiftably engaged with side surfaces of the respective recess. The leaflets have a beveled bottom surface having two separate planar surfaces which lie at an angle to one another. A central region of each leaflet is spaced apart from the annular base when the leaflet is in a fully closed position to minimize cavitation.

As it is well known, tilting leaflet heart valves operate in a rotational motion. These valves may include one leaflet, two leaflets (bi-leaflet) or possibly three leaflets. The leaflet rotates about an axis displaced from the centerline of the valve housing. When the leaflet rotates to a closed position in the housing, the contact between the leaflet and the housing usually occurs at a single point. As illustrated in the references above, some valves have a simple point contact along the housing wall and others have an overlapping surface contact.

The leaflets can fail due to cavitation. This occurs because the leaflet moves at a very high velocity as blood is pumped through the valve. The blood adjacent the valve closure point wants to continue to move after valve closure occurs. Thus, a low pressure region is created adjacent the valve contact point. If the low pressure region reaches a minus 760 mm Hg, i.e. 1 atmosphere, cavitation occurs creating a bubble in the blood which subsequently implodes causing cavitation erosion of any adjacent surface such as a surface of the valve. Factors involved with cavitation include the velocity of the moving leaflet and the valve contact geometry.

From a performance standpoint, it is desirable to have a valve which closes quickly to reduce the quantity of blood flowing in the retrograde direction. This is dependent on the velocity factor. The single point of contact between the leaflet and the valve housing occurs at the farthest distance from the axis of rotation of the leaflet. Therefore, the point of contact had the highest linear velocity of any point on the leaflet, thus increasing the likelihood of cavitation. The single point of contact is near the center of the peripheral edge of the leaflet, i.e. the leaflet major radius (MR).

Cavitation erosion occurs near the MR on the inflow side of the leaflet and at an adjacent location on the housing. The faster the leaflet is moving just before impact, the higher the rate of deceleration. When the leaflet decelerates too quickly, the inertia of the blood causes it to separate from the surface of the leaflet resulting in the above-described low pressure region and causing the bubble to form. Thus, the cavitation erosion damage occurs in a location which is downstream (during reverse flow) of the leaflet/housing orifice contact upon closure.

Therefore, in view of the limitations of past developments, what is needed is a tilting leaflet valve which moves the contact point away from the MR without an unacceptable increase in the amount of the leakage during valve closure.

SUMMARY

One embodiment, accordingly, provides a tilting leaflet valve with one or more leaflets wherein there is no contact between the leaflet and the housing at the center of the MR. To this end, a heart valve includes a valve housing having an opening having an inmost tubular surface of a first curvature. A pivotal leaflet is mounted in the valve for movement between an open position and a closed position with the housing. The leaflet has a second curvature providing multiple points of contact between a peripheral edge of the leaflet and the inmost tubular surface of the valve housing.

A principal advantage of this embodiment is that a leakage gap is provided at the center of the MR thus reducing cavitation erosion. The gap is between multiple points of contact between a peripheral edge of the leaflet and the housing.

DETAILED DESCRIPTION

Figure 1:
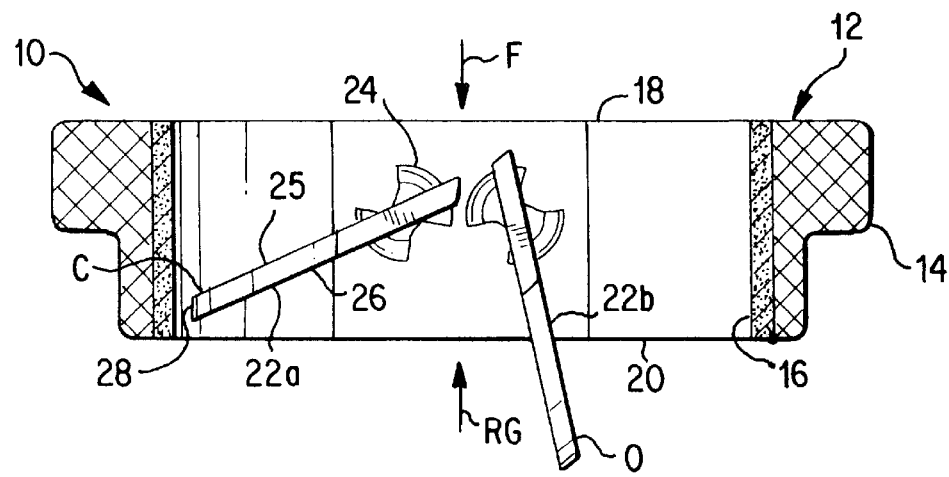
FIG. 1 is a cross-sectional view illustrating an embodiment of a heart valve prosthesis taken along line 1—1 of FIG. 2.

A heart valve prosthesis is generally designated 10, FIG. 1 and includes a valve housing 12 having an outer arcuate brim 14, an inmost arcuate surface 16 of a generally tubular shape, an inlet 18 and an outlet 20. Arcuate surface 16 extends from inlet 18 to outlet 20. Housing 12 is preferably formed of polyester knit cloth material, and inmost arcuate surface 16 is preferably formed of pyrolytic carbon material. At least one leaflet 22a is pivotally mounted at 24 in housing 12 for pivoting between an open position O and a closed position C. Preferably a pair of leaflets 22a and 22b are mounted in housing 12 for pivoting outward to open position O, and pivoting inward to the closed position C. In some instances, a single disk or tri-leaflet valve may be provided.

Figure 2:
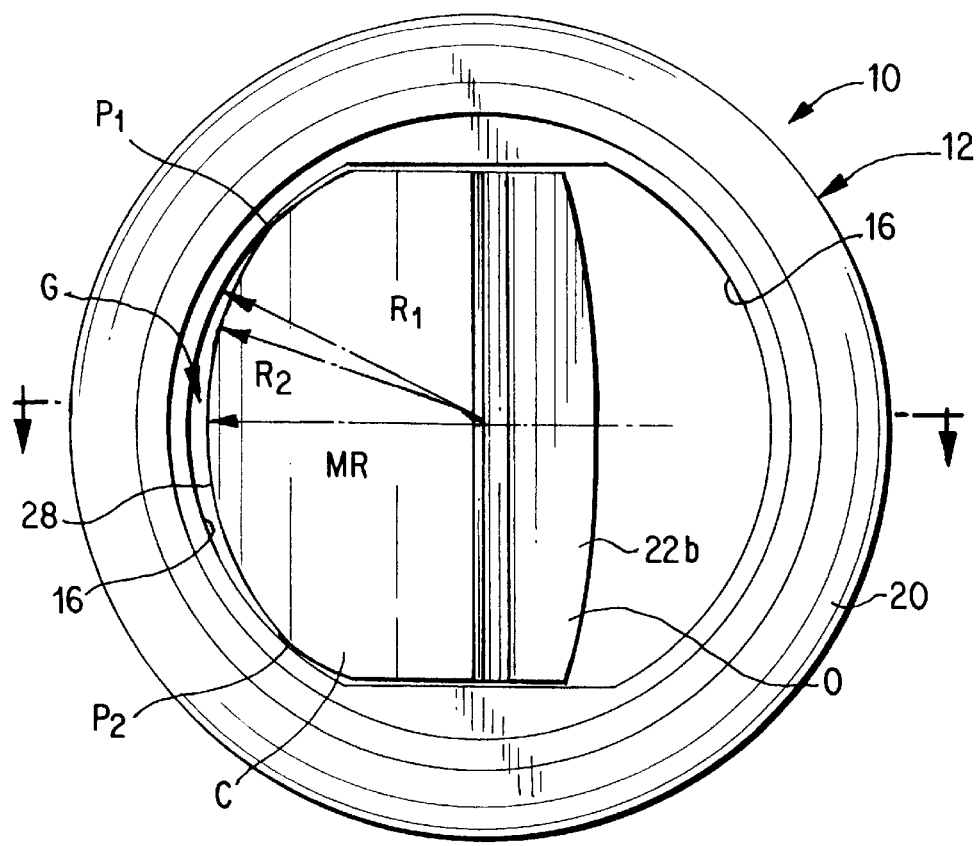
FIG. 2 is a view illustrating an embodiment of a heart valve prosthesis as viewed at the downstream face or outlet.

Each leaflet 22a and 22b is preferably formed of pyrolytic carbon coating over a graphite leaflet substrate material, and includes an upstream surface 25, a downstream surface 26 and a peripheral edge 28. Arcuate surface 16, FIG. 2, includes a first curvature $R_1$ and peripheral edge 28 includes a second curvature $R_2$ which is which is sufficiently different from curvature $R_1$ so that peripheral edge 28 engages arcuate surface 16 only at multiple points of contact $P_1$ and $P_2$ when the leaflet 22a is in closed position C. As a result, a leakage gap G is formed by a spaces defined between peripheral edge 28 and arcuate surface 16 and is between, or separates, the multiple points of contact $P_1$ and $P_2$ The gap G is adjacent a leaflet major radius designated MR and the width of the gap G is preferably in the range of from about 0.001 inches to about 0.008 inches.

Fluid flow is directed though valve 10 in the direction of a directional arrow designated F, from the inlet 18 to the outlet 20. Fluid impinges on the upstream surface 25 of each leaflet 22a and 22b and pivots the leaflet to open position O. Due to the pumping action of the heart, leaflets 22a and 22b rotate quickly back to the closed position C in response to fluid flow in the retrograde direction, i.e. back toward the inlet 18 in the direction of a directional arrow designated RG. Upon closure, each leaflet contacts the arcuate surface 16 at the multiple contact points $P_1$ and $P_2$, FIG. 2. The point contact does not occur at a single point, i.e. the leaflet major radius MR, where the highest linear velocity of each leaflet 22a and 22b, and thus, a higher rate of deceleration occurs. As a result, cavitation erosion damage is minimized because the contact points $P_1$ and $P_2$ are removed from the leaflet major radius MR and the adjacent curved surfaces, i.e. arcuate surface 16 and peripheral edge 28, define an acceptable increase in the amount of leakage at the leakage gap G during valve closure.

Figure 3:
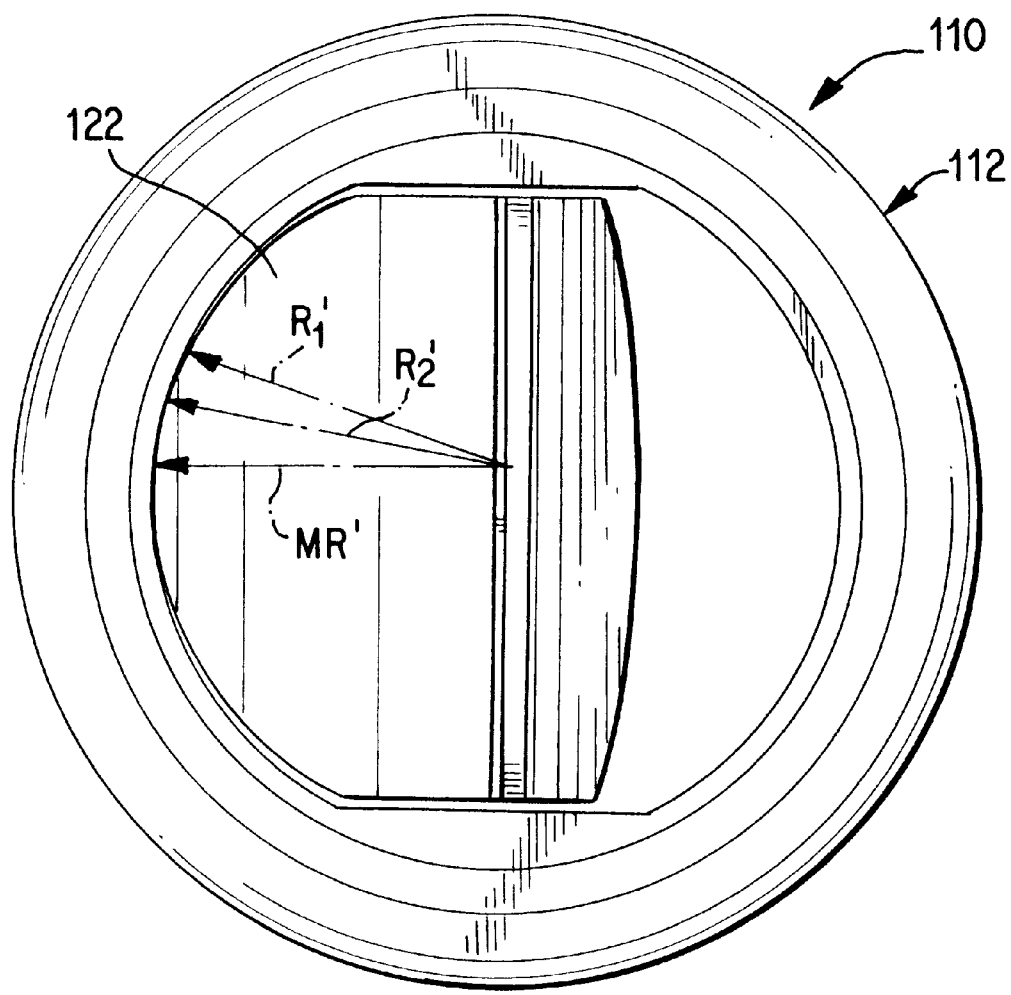
FIG. 3 is a view illustrating an embodiment of a prior art heart valve prosthesis.

This is in substantial contrast to current valves, FIG. 3, wherein the curvatures $R_1$ and $R_2$ are substantially the same so that contact between a housing 112 and a leaflet 122 occurs at the major radius MR where the highest linear velocity of leaflet 122 also occurs in response to fluid flow in the retrograde direction, thus maximizing cavitation erosion damage.

As a result, one embodiment provides a heart valve prosthesis 10 including a housing 12 having an opening formed therein which has an inmost tubular surface 16 of a first curvature $R_1$. A leaflet 22a is pivotally mounted in the opening for movement between an open position O and a closed position C with the housing 12. The leaflet 22a has a peripheral edge 28 including a second curvature $R_2$ which is different from the first curvature $R_1$. This provides multiple points of contact $P_1$ and $P_2$ between the peripheral edge 28 of the leaflet 22a and the inmost tubular surface 16 of the valve housing 12.

Another embodiment provides a pivoting leaflet heart valve prosthesis 10 including a valve housing 12 having an opening formed therein which has an inmost arcuate surface 16. A leaflet 22a is pivotally mounted in the opening for movement between an open position O and a closed position C with the inmost arcuate surface 16. The leaflet 22a includes a peripheral edge 28 providing multiple points of contact $P_1$ and $P_2$ between the peripheral edge and the inmost arcuate surface 16. The multiple points of contact $P_1$ and $P_2$ provide a leakage gap G therebetween.

Another embodiment provides a multi-leaflet heart valve prosthesis 10 including a valve housing 12 having an opening formed therein and an inmost arcuate surface 16. A plurality of leaflets 22a and 22b are pivotally mounted in the opening for movement between an open position O and a closed position C with the inmost arcuate surface 16. Each leaflet 22a and 22b has an outmost edge 28 providing multiple points of contact $P_1$ and $P_2$ with the inmost arcuate surface 16. Each leaflet 22a and 22b forms a leakage gap G between the outmost edge 28 and the inmost arcuate surface 16. The leakage gap G is between the multiple points of contact $P_1$ and $P_2$.

A further embodiment provides a method of providing leaflet closure in a heart valve prosthesis 10 by providing a valve housing 12 having an opening formed therein including an inmost arcuate surface 16. A leaflet 22a has a peripheral edge 28. Multiple points of contact $P_1$ and $P_2$ are provided between the peripheral edge 28 and the inmost arcuate surface 16. A leakage gap G is provided at the peripheral edge 28 separating the multiple points of contact $P_1$ and $P_2$. The leaflet 22a is mounted in the valve 10 for pivotal movement between an open position O and a closed position C so that when the multiple points of contact $P_1$ and $P_2$ engage the inmost arcuate surface 16 in the closed position C, the leakage gap G is maintained between the peripheral edge 28 and the inmost arcuate surface 16.

As it can be seen, the principal advantages of these embodiments are that in a tilting disk heart valve with one or more occluders, there is no contact between the leaflet major radius MR and the gap G near the center of the major radius MR. The leakage gap G is provided at the center of the major radius MR thus reducing cavitation erosion. The gap is between multiple points $P_1$ and $P_2$ of contact between a peripheral edge of the leaflet and the housing.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A heart valve prosthesis comprising:
    a valve housing having an opening formed therein, an inlet, an outlet, and an inmost arcuate surface having a first curvature and a generally tubular shape extending from the inlet to the outlet;
    a leaflet pivotally coupled to said valve housing for movement between an open position and a closed position, said leaflet having an upstream surface, a downstream surface, and a peripheral edge comprising a second curvature, different from the first curvature, wherein in said closed position the peripheral edge of the leaflet engages the inmost arcuate surface of the valve housing at multiple points of contact, and provides a leakage gap between the inmost arcuate surface and the peripheral edge of the leaflet.

2. The heart valve prosthesis of claim 1 wherein said leakage gap has a width of between about 0.001 and 0.008 inches.

3. The heart valve as defined in claim 1 wherein the leaflet includes a major radius, the leakage gap being adjacent the major radius.

4. A pivoting leaflet heart valve prosthesis comprising:
    a valve housing having an opening formed therein, an inlet, an outlet, and an inmost arcuate surface extending from the inlet to the outlet;
    a leaflet pivotally coupled to said valve housing for movement between an open position and a closed position, said leaflet having an upstream surface, a downstream surface, and a peripheral edge, wherein in said closed position the peripheral edge of the leaflet engages the inmost arcuate surface of the valve housing at multiple points of contact between the peripheral edge and the inmost arcuate surface, the multiple points of contact providing a leakage gap having a width of from about 0.001 to about 0.008 inches between said peripheral edge and said inmost arcuate surface.

5. The heart valve as defined in claim 4 wherein the leaflet includes a major radius adjacent the leakage gap.

6. The heart valve as defined in claim 4 wherein the multiple points of contact engage the inmost arcuate surface between the inlet and the outlet and displaced from the major radius.

7. A method of providing leaflet closure in a heart valve prosthesis comprising the steps of:
    providing a valve housing having an opening formed therein including an inlet, an outlet, and an inmost arcuate surface;
    providing a leaflet having an upstream surface, a downstream surface, and a peripheral edge;
    providing multiple points of contact between the peripheral edge and the inmost arcuate surface;
    providing a leakage gap at the peripheral edge separating the multiple points of contact; and
    coupling the leaflet to the valve housing for movement between an open position and a closed position, such that when the peripheral edge engages the inmust surface to provide the multiple points of contact in the closed position, the leakage gap is maintained between the peripheral edge and the inmost arcuate surface.

8. The method as defined in claim 7 wherein the step of forming includes the step of providing a major radius on the leaflet.

9. The method of claim 7, wherein the leakage gap has a width of from about 0.001 to about 0.008 inches.

10. The method as defined in claim 9 wherein the step of mounting the leaflet includes the step of engaging the inmost arcuate surface between the inlet and outlet.

* * * * *